United States Patent [19]

Drent

[11] Patent Number: 4,640,802
[45] Date of Patent: Feb. 3, 1987

[54] PROCESS FOR THE CO-PRODUCTION OF CARBOXYLIC ACIDS AND CARBOXYLIC ACID ESTERS

[75] Inventor: Eit Drent, Amsterdam, Netherlands

[73] Assignee: Shell Oil Company, Houston, Tex.

[21] Appl. No.: 395,952

[22] Filed: Jul. 7, 1982

[30] Foreign Application Priority Data

Dec. 10, 1981 [GB] United Kingdom ............... 8137359

[51] Int. Cl.$^4$ ...................... C07C 51/12; C07C 67/36; C07C 67/37
[52] U.S. Cl. ............... 260/410.9 R; 260/408; 260/410.5; 260/413; 260/410.6; 560/51; 560/55; 560/64; 560/72; 560/73; 560/75; 560/103; 560/105; 560/106; 560/111; 560/112; 560/175; 560/187; 560/226; 560/227; 560/232; 560/234; 560/240; 560/265; 562/406; 562/517; 562/606; 562/607
[58] Field of Search ............... 560/232, 265, 105, 106, 560/103, 111, 112, 75, 175, 227, 187, 226, 51, 560/55, 64, 73, 204, 72; 562/517, 406, 497, 606, 607; 260/413, 408, 410.9 R, 410.5; 410.6

[56] References Cited

U.S. PATENT DOCUMENTS 4,189,441  2/1980  Braca et al. .................. 560/232
4,190,729  2/1980  Forster ....................... 560/232

Primary Examiner—Vivian Garner
Attorney, Agent, or Firm—Ronald R. Reper

[57] ABSTRACT

Process for the co-production of carboxylic acids of the general formula $R^1$—COOH and $R^2$—COOH and carboxylic acid esters of the general formula $R^1$—COOCH$_2$R$^2$ and $R^2$—COOCH$_2$R$^1$ from carboxylic acid esters of the general formula $R^1$—COOR$^2$ and/or ethers of the general formula $R^3$OR$^4$ ($R^1$, $R^2$, $R^3$, $R^4$ representing (substituted) alkyl or (substituted) aryl, alkaryl or aralkyl, $R^1$ also representing H), carbon monoxide and hydrogen at elevated temperature and pressure in the presence of a ruthenium compound, a further Group VIII metal compound, a phosphine oxide and a compound $R^5$Hal or $R^5$COHal where $R^5$ has one of the meanings given for $R^2$ and Hal is iodine or bromine, the reaction mixture being substantially free from other transition metal or Group II metal iodides or bromides, and containing a tertiary phosphine oxide. The process is of special interest for the selective conversion of methyl acetate into ethyl acetate and acetic acid at pressure well below 100 bar.

20 Claims, No Drawings

PROCESS FOR THE CO-PRODUCTION OF CARBOXYLIC ACIDS AND CARBOXYLIC ACID ESTERS

FIELD OF THE INVENTION

This invention relates to a process for the co-production of carboxylic acids and carboxylic acid esters from carboxylic acid esters or ethers, carbon monoxide and hydrogen in the presence of a homologation catalyst system.

BACKGROUND OF THE INVENTION

The production of carboxylic acid esters via homologation has already been described in the literature.

It is known from European Patent Application No. 31606 that the stoichiometry of the known reactions of methyl acetate with carbon monoxide and hydrogen can be altered most advantageously to produce one mole of ethyl acetate and two moles of acetic acid from two moles of methyl acetate. The catalytic system comprises three metal compounds: a ruthenium compound, a further Group VIII metal compound, and a bromide or iodide of a Group II or transition metal, preferably in the presence of a promoter, typically an amine or a phosphine.

It has been described and claimed in our co-pending Application Ser. No. 395,496, filed July 7, 1982, now abandoned, that an alkyl or acyl iodide or bromide can replace the Group II or transition metal iodide or bromide in the catalytic system as disclosed in European Patent Application No. 31606, provided that the reaction is carried out in the presence of a phosphine in an amount not exceeding a certain level.

SUMMARY OF THE INVENTION

The present invention relates to a process for the co-production of carboxylic acids and carboxylic acid esters from carboxylic acid esters having one carbon atom less in the molecule, carbon monoxide and hydrogen in the presence of a catalytic system. The invention relates in particular to a process for the co-production of acetic acid and ethyl acetate from methyl acetate under mild process conditions. Carboxylic acid esters produced according to the process according to the present invention are thus homologs of the carboxylic acid esters used as starting materials.

It has been found that phosphine oxides can also be applied advantageously in the process for the co-production of carboxylic acids and carboxylic acid esters using a catalytic system based on a ruthenium compound, a further Group VIII metal compound and an alkyl or acyl iodide or bromide.

DESCRIPTION OF THE PREFERRED EMBODIMENTS

The present invention provides a process for the co-production of carboxylic acids of the general formula $R^1$—COOH and $R^2$—COOH and carboxylic acid esters of the general formula $R^1$—COOCH$_2R^2$ and $R^2$—COOCH$_2R^1$ wherein each of the groups $R^1$ and $R^2$, which may be the same or different, represents an alkyl group having from 1 to 20 carbon atoms which may be substituted by one or more inert substituents such as fluorine or chlorine-containing moieties or hydroxy, alkoxy or alkanoyl groups, or an aryl, alkaryl or aralkyl group having up to about 20 carbon atoms which may be substituted by one or more inert substituents such as fluorine or chlorine-containing moieties or alkoxy or alkanoyl groups, while $R^1$ may also represent a hydrogen atom, wherein a carboxylic acid ester of the general formula $R^1$—COOR$^2$ and/or an ether of the general formula $R^3OR^4$, wherein $R^1$ and $R^2$ are as defined hereinbefore and each of $R^3$ and $R^4$, which may be the same or different, represents an alkyl group having from 1 to 20 carbon atoms which may be substituted by one or more inert substituents such as fluorine or chlorine-containing moieties or hydroxy, alkoxy or alkanoyl groups, or an aryl, alkaryl or aralkyl group having up to about 20 carbon atoms which may be substituted by one or more inert substituents such as fluorine or chlorine-containing moieties or alkoxy or alkanoyl groups, is reacted with carbon monoxide and hydrogen at elevated temperature and pressure in the presence of a catalytic system which comprises a ruthenium compound, a further Group VIII metal compound, a phosphine oxide and a compound of the general formula $R^5$Hal or $R^5$COHal where $R^5$ has one of the meanings given above for $R^2$ and Hal represents an iodine or bromine atom, the reaction mixture being substantially free from other transition metal or Group II metal iodides or bromides.

It should be noted that the composition of the reaction product mixture will be governed by the choice of the starting carboxylic acid esters and/or ethers. For instance, when starting materials are used wherein the groups $R^1$ and $R^2$ are identical, such as in methyl acetate, dimethyl ether and ethyl propionate, the reaction product mixture will normally contain only the carboxylic acid ester homolog and the appropriate acid. When starting materials are used wherein the groups $R^1$ and $R^2$ are not identical, a more complex reaction product mixture will be obtained which comprises normally at least two carboxylic acid ester homologs and two appropriate carboxylic acids. For instance, when ethyl acetate is used as the starting material the reaction product mixture comprises propyl acetate, ethyl propionate, propionic acid and acetic acid.

It will be appreciated that any carboxylic acid ester homolog produced according to the present process can serve as starting material in the process according to the present invention, thus forming the next carboxylic acid ester homolog(s) and the appropriate carboxylic acid(s). In addition, since carboxylic acids are produced in the process according to the present invention, transesterification reactions, i.e. reactions between carboxylic acids and carboxylic acid esters, or between different carboxylic acid esters, may also occur under the prevailing reaction conditions. It will be clear that transesterification reactions do not alter the product composition when the starting material comprises compounds wherein $R^1$ and $R^2$ are identical, but may alter the product composition when the groups $R^1$ and $R^2$ are not identical.

For the purpose of the present invention, carboxylic acids and carboxylic acid esters, obtained via a further homologation of produced carboxylic acid ester, or obtained by a transesterification process under the prevailing conditions, are considered to be within the scope of the present invention.

From the above it will be clear that preference is given to processes wherein starting materials are used wherein the groups $R^1$ and $R^2$ are identical since a less complex reaction mixture will be obtained. The process according to the present invention is of special interest for the coproduction of acetic acid and ethyl acetate from methyl acetate according to the equation: $2CH_3COOCH_3 + 2CO + 2H_2 \rightarrow CH_3COOC_2H_5 + 2CH_3COOH$, since the products can be obtained with high selectivity and close to the stoichiometrically expected ratio. This is of special interest when the Process according to the invention is part of an integrated process, wherein acid produced—for instance, acetic acid—is to be recycled in the process. Moreover, the process according to the present invention can be carried out conveniently at surprisingly low pressures, e.g. pressures well below 100 bar can be used advantageously.

Suitable starting materials which can be used conveniently in the process according to the present invention include compounds of the general formula $R^1$—$COOR^2$ and/or $R^3OR^4$, wherein each of $R^1$, $R^2$, $R^3$ and $R^4$, which may be the same or different, represents an alkyl group having from 1 to about 12 carbon atoms, or an aryl, alkaryl or aralkyl group having up to about 12 carbon atoms, while $R^1$ may also represent a hydrogen atom. Preference is given to the use of compounds of the general formula $R^1$—$COOR^2$ and/or $R^3OR^4$, wherein $R^1$, $R^2$, $R^3$ and $R^4$ are the same, and each represents an alkyl group having from 1 to about 12 carbon atoms or an aryl, alkaryl or aralkyl group having up to about 12 carbon atoms. Most preferred starting materials are methyl acetate and dimethyl ether.

When ethers of the general formula $R^3OR^4$ are used as starting materials in the process according to the present invention, it would appear that these compounds will be converted primarily into the corresponding esters by the introduction of a carbon monoxide moiety into the molecule, which molecule may then undergo the homologation reaction according to the present invention. If desired, the reaction according to the present invention may be carried out in two stages when an ether is used as the starting material. Firstly, the ether is converted into the corresponding ester which in its turn, in the same or in a different vessel, is converted into the final products. If desired, mixtures of carboxylic acid esters and/or ethers can be used as starting materials.

Ruthenium compounds which can be used conveniently in the process according to the present invention include ruthenium(III) chloride, ruthenium(III) chloride trihydrate, ruthenium(IV) chloride, ruthenium(III) bromide, the ruthenium oxides, organic ruthenium salts such as ruthenium(III) propionate, ruthenium(III) butyrate, ruthenium pentacarbonyl, triruthenium dodecacarbonyl and mixed ruthenium halocarbonyls such as bis-[rutheniumtricarbonyldibromide), and other organoruthenium complexes.

Further Group VIII metal compounds which can be used together with a ruthenium compound in the catalytic system include palladium and, especially, rhodium compounds, although other Group VIII metal compounds can also be used. Examples of suitable rhodium compounds include rhodium oxide, rhodium(III) hydroxide, rhodium(III) chloride, rhodium(III) chloride trihydrate, rhodium(III) bromide, rhodium(III) iodide and the corresponding pyridine and phosphine complexes such as tris(pyridine) rhodium(III) chloride or dichloro bis-(triphenylphosphine) rhodium, rhodium(III) formate, rhodium(III) acetate, rhodium(III) butyrate, rhodium(III) naphthenate, dirhodium octacarbonyl, tetrarhodium dodecacarbonyl, hexarhodium hexadecacarbonyl, rhodium dicarbonylacetylacetonate and other organo-rhodium complexes. Preference is given to the use of rhodium(III) chloride trihydrate.

Examples of suitable palladium compounds include palladium chloride, palladium chloride dihydrate, palladium bromide, palladium iodide, palladium oxide, or an organic palladium salt or complex such as palladium formate, palladium acetate, palladium butyrate and palladium acetylacetonate. Preferred palladium compounds are palladium chloride, palladium chloride dihydrate and palladium acetate.

The molar ratio of ruthenium compound to further Group VIII metal compound is not critical and can vary between wide limits, e.g. atomic ratios of ruthenium to further Group VIII metal between about 50:1 and about 1:20, especially between about 10:1 and 1:5, are suitable.

The amount of ruthenium compound and further Group VIII metal compound to be used is not critical, and any amount which exerts catalytic activity can be used. Amounts as low as about 0.001% w, calculated on carboxylic acid ester or ether to be converted can be used, preference being given to amounts in the range of from about 0.01–10% w, most preferably between about 0.05–5% w.

Any iodide or bromide $R^5Hal$ or $R^5COHal$ may be used in the process according to the present invention, but preferably $R^5$ has one of the preferred meanings given above for $R^2$, and preferably the group $R^5$ is identical to one of the groups $R^1$, $R^2$, $R^3$ or $R^4$ in the starting material, as this avoids the formation of additional mixed products. Especially preferred is the use of a reaction mixture in which $R^1$ and $R^2$ are the same, and the iodide or bromide has the formula $R^2I$, $R^2Br$, $R^2COI$ or $R^2COBr$. Thus, for example, when using the preferred feedstocks methyl acetate and/or dimethyl ether, methyl iodide or bromide or acetyl iodide or bromide, or any mixture thereof, is preferably used.

The quantity of iodide or bromide added to the reaction mixture is not crucial. Suitably, the number of moles of added iodide plus bromide per gram atom of total group VIII metal is in the range of from about 0.1:1 to about 200:1, preferably from about 1:1 to about 100:1, and especially from about 10:1 to about 50:1.

As stated hereinbefore, the process according to the present invention is carried out in the presence of a phosphine oxide. Suitable phosphine oxides which can be used include tertiary phosphine oxides according to the general formula $OPR^6R^7R^8$, wherein each of $R^6$, $R^7$ and $R^8$, which may be the same or different, represents a substituted or unsubstituted, alkyl, cycloalkyl or aryl group having up to 20, preferably up to 7 carbon atoms. Also, tertiary phosphine oxides containing two or more phosphorus atoms can be used as well as the corresponding oxy-acid derivatives according to the general formula $OP(OR^6)(OR^7)(OR^8)$, wherein $R^6$, $R^7$ and $R^8$ each has the meanings as defined hereinabove. It is further possible to use phosphonates, i.e. compounds according to the general formula $OP[(O)_aR^6][(O)_bR^7][(O)_cR^8]$ wherein a, b and c are 0 or 1 and $a+b+c$ is 1 or 2 and $R^6$, $R^7$ and $R^8$ have the meanings as defined hereinabove.

Examples of phosphine oxides include trimethylphosphineoxide, triethylphosphineoxide, tri-n-butylphosphineoxide, triphenylphosphineoxide, tri-p-tolylphosphineoxide, tetraphenyl dimethylene diphosphine dioxide (diphosdioxide) and tetraphenyl trimethylene diphosphine dioxide. Preference is given to the use of triphenylphosphine oxide.

Examples of compounds according to the general formula $OP(OR^6)(OR^7)(OR^8)$ comprise the alkyl and aryl esters of phosphoric acid such as trimethyl phosphate, triethyl phosphate, tri-n-butylphosphate and triphenyl phosphate. Examples of suitable phosphonates comprise dimethyl methylphosphonate, diethyl methylphosphonate diphenyl methylphosphonate, methyl dimethylphosphonate, methyl diethylphosphonate and methyl diphenylphosphonate. Also, mixtures of one or more phosphine oxides and/or one or more phosphates can be suitably applied.

The phosphine oxides are present in the reaction mixture in catalytic quantities, but the precise amount is not critical. Suitably, the molar ratio of the phosphine oxide to ruthenium is in the range of from about 0.01:1 to about 20:1, preferably in the range of from about 0.05:1 to about 10:1.

The process according to the present invention can be carried out using a wide range of temperatures. Temperatures up to about 300° C. can be suitably applied. Preference is given to temperatures in the range of from about 50° C. to about 200° C., most preferred temperatures are in the range between about 125° C. and about 175° C.

The process according to the present invention can be carried out using low pressures, e.g. pressures as low as about 5 bar. Pressures in the range of from about 20 to about 100 bar are preferred. Higher pressures, e.g. pressures as high as about 1000 bar can be applied, but they are generally not economical because of the investment and energy costs involved.

According to the reaction equation, carbon monoxide and hydrogen are consumed in a molar ratio of 1:1. It has been found, however, that without any substantial disadvantage wider molar ratios, e.g. ratios of from about 1:10 to about 10:1 can be applied. Preference is given to ratios carbon monoxide:hydrogen in the range of from about 1:0.5 to about 1:3.

The process according to the present invention may be carried out in the presence of a solvent. Suitable solvents include carboxylic acids such as acetic acid or propanoic acid; carboxylic acid esters, such as methyl acetate, ethyl acetate, methyl propionate or ethyl propionate (being used as solvent as well as starting material); and cyclic ethers such as tetrahydrofuran, 1,4-dioxane, 1,3-dioxane and the dioxolanes. Also, dialkyl ethers used in excess as starting material may be regarded as solvent for the process according to the present invention. Suitable dialkyl ethers include dimethyl ether, diethyl ether and methyl t-butyl ether.

Other compounds which can be used as solvent in the process according to the present invention include sulphones and sulphoxides. Examples of such compounds are dimethylsulphone, sulpholane, 2-methyl sulpholane, 3-methyl sulpholane, dimethylsulphoxide and diethyl sulphoxide.

Especially good results are obtained when alkanoic acids such as acetic acid are used as solvent. If, however, a solvent other than an alkanoic acid is used, it may be desirable to carry out the reaction in the presence of small amounts of a strong acid. For example, amounts of strong acid of up to about 100 equivalents of acid per gram atom of total Group VIII metal, may be added. Suitable strong acids include those which in aqueous solution at 20° C. have a pKa of less than 3.5, for example, organic acids such as p-toluene sulphonic acid or trifluoromethane sulphonic acid, or mineral acids such as hydrochloric, sulphuric or perchloric acid.

The mild conditions according to the present invention even tolerate the presence of some water in the reaction medium. Although the presence of water is not preferred, amounts of up to about 15% w, based on total solvent, may be present.

The process according to the present invention can be carried out in the liquid phase or in the gaseous phase. Preference is given to a liquid phase which enables a convenient introduction of carbon monoxide and hydrogen into the reaction vessel. If desired, the carbon monoxide and hydrogen can be introduced together into the reaction vessel. The process according to the present invention can be carried out batchwise, semi-continuously or continuously.

The process according to the present invention is also of interest in that it can be integrated with known processes, either for the production of the starting materials (i.e. carboxylic acid esters or the corresponding ethers) or for the conversion of the carboxylic acid esters produced into other products, e.g. by transesterification processes. For instance, when the present process produces ethyl acetate, it can be integrated with a process for the preparation of methyl acetate from acetic acid and methanol using an acidic catalyst. Since the present process produces acetic acid, that compound may be recycled to serve as feedstock for the preparation of methyl acetate. If desired, the present process can also be integrated with a transesterification process, wherein ethyl acetate is transesterified with methanol to give methyl acetate (which can be recycled to serve as feedstock for the present process) and ethanol which can either be sold as such or converted into other products such as ethylene. In such a case acetic acid and/or methyl acetate can be removed from the system in an amount equimolar with ethanol produced.

The following Examples are provided to illustrate the invention and are not to be construed as limiting the invention.

EXAMPLE I

The experiment was carried out in a 300 ml magnet-driven autoclave of Hastelloy C (trademark) which contained 25 ml methyl acetate, 25 ml acetic acid, 60 mmol methyl iodide, 0.12 mmol rhodium(III) chloride trihydrate, 1 mmol ruthenium(III) chloride trihydrate and 4 mmol triphenylphosphineoxide. The vessel was pressurized with carbon monoxide (20 bar partial pressure) and hydrogen (40 bar partial pressure). The autoclave was then heated to 160° C. and kept at this temperature for 5 hours. After this time the reaction mixture was analyzed by gas-liquid chromatography and shown to contain 22.1% w ethyl acetate. On a molar basis the conversion of the starting material was about 90%, with an almost 100% selectivity towards the two products, ethyl acetate and acetic acid. Only traces (less than 0.5%) of by-products were detected; in particular, no alcohols were detected.

EXAMPLE II

The method of Example I was repeated except that an additional 0.5 mmol rhodium(III) chloride trihydrate and only 15 mmol methyl iodide were used. After the reaction time was over, the reaction mixture contained 14.6% w ethyl acetate, and 55% of the methyl acetate had been converted to the desired products. Only traces of by-products were observed.

I claim:

1. A process for the co-production of carboxylic acids of the general formula $R^1$—COOH and $R^2$—COOH, and carboxylic acid esters of the general formula $R^1COOCH_2R^2$ and $R^2COOCH_2R^1$, wherein each of the groups $R^1$ and $R^2$, which may be the same or different, represents and alkyl group having from 1 to about 20 carbon atoms which may be substituted by one or more inert substituents selected from the group consisting of fluorine or chlorine-containing moieties or hydroxy, alkoxy or alkanoyl groups, or an aryl, alkaryl or aralkyl group which may be substituted by one or more inert substituents selected from the group consisting of fluorine or chlorine-containing moieties or alkoxy or alkanoyl groups, while $R^1$ may also represent a hydrogen atom, characterized in that a carboxylic acid ester of the general formula $R^1$—$COOR^2$ and/or ether of the general formula $R^3OR^4$, wherein $R^1$ and $R^2$ are as defined hereinbefore and each of $R^3$ and $R^4$, which may be the same or different, represents an alkyl group having from 1 to about 20 carbon atoms which may be substituted by one or more inert substituents selected from the group consisting of fluorine or chlorine-containing moieties or hydroxy, alkoxy or alkanoyl groups, or an aryl, alkaryl or aralkyl group which may be substituted by one or more inert substituents selected from the group consisting of fluorine or chlorine-containing moieties or alkoxy or alkanoyl groups, is reacted with carbon monoxide and hydrogen at a temperature of up to about 300° C. and a pressure of up to about 1000 bar in the presence of a catalytic system which comprises a ruthenium compound and a further compound of a Group VIII metal selected from the group consisting of rhodium and palladium, and a compound of the general formula $R^5Hal$ or $R^5COHal$ where $R^5$ has one of the meanings given above for $R^2$ and Hal represents an iodine or bromine atom, the reaction mixture being substantially free from other transition metal or Group II metal iodides or bromides, and containing a tertiary phosphine oxide according to the general formula $OPR^6R^7R^8$, wherein each of $R^6$, $R^7$ and $R^8$, which may be the same or different, represents a substituted or unsubstituted alkyl, cycloalkyl or aryl group having up to 20 carbon atoms, a tertiary phosphine oxide containing two or more phosphorus atoms or the corresponding oxy-acid derivatives according to the general formula $OP(OR^6)(OR^7)(OR^8)$ wherein $R^6$, $R^7$ and $R^8$ each has the meanings as defined hereinabove or phosphonates according to the general formula $OP[(O)_aR^6][(O)_bR^7][(O)_cR^8]$ wherein a, b and c are 0 or 1 and a+b+c is 1 or 2 and $R^6$, $R^7$ and $R^8$ have the meanings as defined hereinbefore.

2. The process according to claim 1 characterized in that as starting materials are used compounds of the general formula $R^1$—$COOR^2$ and/or $R^3OR^4$, wherein each of $R^1$, $R^2$, $R^3$ and $R^4$, which may be the same or different, represents an alkyl group having from 1 to about 12 carbon atoms or an aryl, alkaryl or aralkyl group having up to about 12 carbon atoms, while $R^1$ may also represent a hydrogen atom.

3. The process according to claims 1 or 2 wherein the ruthenium compound is selected from the group consisting of ruthenium(III) chloride, ruthenium(III) chloride trihydrate, ruthenium(IV) chloride, ruthenium(III) bromide, ruthenium oxide, or mixture thereof.

4. The process according to claims 1 or 2 wherein the further Group VIII metal compound is a rhodium compound.

5. The process according to claims 1 or 2 wherein the further Group VIII metal compound is selected from the group consisting of rhodium oxide, rhodium(III) hydroxide, rhodium(III) chloride, rhodium(III) chloride trihydrate, rhodium(III) bromide, rhodium(III) iodide, an organic rhodium salt, an organic rhodium complex or mixtures thereof.

6. The process according to claims 1 or 2 wherein the further Group VIII metal compound is rhodium(III) chloride trihydrate.

7. The process according to claims 1 or 2 wherein the further Group VIII metal compound is selected from the group consisting of palladium chloride, palladium chloride dihydrate, palladium bromide, palladium iodide, palladium oxide, or mixtures thereof.

8. The process according to claims 1 or 2 wherein the further Group VIII metal compound is selected from the group consisting of palladium chloride, palladium chloride dihydrate, palladium acetate or mixtures thereof.

9. The process according to claims 1 or 2 wherein the ruthenium compound and the further Group VIII metal compound are used in a ratio between about 50:1 and about 1:20.

10. The process according to claims 1 or 2 wherein the ruthenium compound and the further Group VIII metal compound are used in a ratio between about 10:1 and about 1:5.

11. The process according to claims 1 or 2 wherein the group $R^5$ is identical to one of the groups $R^2$, $R^3$ or $R^4$ in the starting material.

12. The process according to claim 1 wherein each of $R^6$, $R^7$ and $R^8$ have up to 7 carbon atoms.

13. The process according to claim 1 wherein use is made of trimethylphosphineoxide, triethylphosphineoxide, tri-n-butylphosphineoxide, triphenylphosphineoxide, tri-p-tolylphosphineoxide, tetraphenyl dimethylene diphosphinedioxide or tetraphenyl trimethylene diphosphinedioxide.

14. The process according to claim 13 where use is made of triphenyl phosphineoxide.

15. The process according to claims 1, 2, 12, 13 or 14 wherein use is made of a phosphine oxide:ruthenium molar ratio in the range of from about 0.01:1 to about 20:1.

16. The process according to claims 1, 2, 12, 13 or 14 wherein use is made of a phosphine oxide:ruthenium molar ratio in the range of from about 0.05:1 to about 10:1.

17. The process according to claims 1 or 12 wherein the reaction is carried out at a temperature in the range of from about 50° C. to about 200° C.

18. The process according to claims 1 or 12 wherein the reaction is carried out at a temperature in the range of from about 125° C. to about 175° C.

19. The process according to claims 1 or 12 wherein the process is carried out at a pressure between about 20 and about 100 bar.

20. The process according to claims 1 or 12 wherein an alkanoic acid is used as a solvent.

* * * * *